(12) United States Patent
Rose et al.

(10) Patent No.: US 9,641,808 B2
(45) Date of Patent: May 2, 2017

(54) NAVIGATING ATTACHMENT FOR OPTICAL DEVICES IN MEDICINE, AND METHOD

(75) Inventors: Andreas Rose, Oberkramer (DE); Timo Kruger, Berlin (DE)

(73) Assignee: FIAGON GMBH, Berlin (DE)

( * ) Notice: Subject to any disclaimer, the term of this patent is extended or adjusted under 35 U.S.C. 154(b) by 266 days.

(21) Appl. No.: 13/881,770

(22) PCT Filed: Oct. 28, 2011

(86) PCT No.: PCT/EP2011/069065
§ 371 (c)(1),
(2), (4) Date: Jun. 10, 2013

(87) PCT Pub. No.: WO2012/056034
PCT Pub. Date: May 3, 2012

(65) Prior Publication Data
US 2013/0258079 A1    Oct. 3, 2013

(30) Foreign Application Priority Data

Oct. 28, 2010   (DE) .................. 10 2010 049 702

(51) Int. Cl.
*A62B 1/04*      (2006.01)
*H04N 7/18*      (2006.01)
(Continued)

(52) U.S. Cl.
CPC .............. *H04N 7/183* (2013.01); *A61B 90/36* (2016.02); *A61B 2017/00296* (2013.01);
(Continued)

(58) Field of Classification Search
CPC ........................................................ H04N 7/18
(Continued)

(56) References Cited

U.S. PATENT DOCUMENTS

2005/0215854 A1*  9/2005  Ozaki ............... A61B 1/00009
                                                           600/109
2008/0071142 A1   3/2008  Gattani et al.
(Continued)

FOREIGN PATENT DOCUMENTS

WO    2007115825 A1    10/2007
WO    2008076079 A1     6/2008
WO    2008095068 A1     8/2008

OTHER PUBLICATIONS

Jing, C et al. "Navigating System for Endoscopic Sinus Surgery Based on Augmented Reality" 2007 IEEE/ICME International Conference on Complex Medical Engineering pp. 185-188. This paper pertains to a medical navigation system which uses an endoscope augmented with CT scan data.*

(Continued)

*Primary Examiner* — Chikaodili E Anyikire
(74) *Attorney, Agent, or Firm* — Ware, Fressola, Magurie & Barber LLP (57) ABSTRACT

A method for presenting image data, in which an optical implement captures the position and positional information is obtained thus and, with the aid of the positional information, image data are determined and displayed or processed further. The image data to be displayed are at least in part based on virtual image data, not real image data captured directly by the optical implement. These virtual image data represent an object or body part situated in the field of view of the optical implement. Within the scope of the method, real image data are recorded by means of the optical implement, the position and/or alignment of the optical implement is captured simultaneously and positional information is derived therefrom.

14 Claims, 3 Drawing Sheets

(51) Int. Cl.
*A61B 90/00* (2016.01)
*A61B 17/00* (2006.01)
*A61B 34/20* (2016.01)

(52) U.S. Cl.
CPC . *A61B 2034/2051* (2016.02); *A61B 2090/364* (2016.02); *A61B 2090/365* (2016.02); *A61B 2090/3612* (2016.02)

(58) Field of Classification Search
USPC .......................................... 348/65; 600/117
See application file for complete search history.

(56) References Cited

U.S. PATENT DOCUMENTS

| | | | |
|---|---|---|---|
| 2008/0218588 A1* | 9/2008 | Stetten | A61B 8/0833 348/47 |
| 2008/0221442 A1* | 9/2008 | Tolkowsky | A61B 6/5217 600/425 |
| 2008/0228188 A1* | 9/2008 | Birkbeck | A61B 17/1703 606/87 |
| 2012/0188352 A1* | 7/2012 | Wittenberg | A61B 19/50 348/65 |

OTHER PUBLICATIONS

Konishi, K. et al. "Augmented reality navigation system for endoscopic surgery based on three-dimensional ultrasound and computed tomography: Application to 20 clinical cases" International Congress Series 1281 (2005) pp. 537-542. This paper pertains to a medical navigation system which uses an endoscope augmented with 3-D ultrasound and CT scan.*

* cited by examiner

Figure 3

NAVIGATING ATTACHMENT FOR OPTICAL DEVICES IN MEDICINE, AND METHOD

CROSS REFERENCE TO RELATED APPLICATIONS

This application is the U.S. National Stage of International Application Number PCT/EP2011/069065 filed on Oct. 28, 2011, which application claims priority under 35 USC §119 to German Patent Application No. 10 2010 049 702.9 filed on Oct. 28, 2010, which applications are hereby incorporated by reference in their entirety.

TECHNICAL FIELD

The invention relates to a method and a device for presenting image data, in which an optical implement captures the position and positional information is obtained thus and, with the aid of the positional information, image data are determined and displayed or processed further.

BACKGROUND OF THE INVENTION

Here, positional information is understood to mean the position and the alignment of the optical implement with respect to a reference coordinate system, i.e. a coordinate system of a position capturing apparatus. The positional information can be captured by means of a position capturing apparatus with a corresponding measurement system.

In many surgical interventions, the surgeon is faced with the problem of orientation within the patient during the operation. Image data of the patient, e.g. computed tomography recordings, often underlie the planning. During the operation, the medical practitioner works having a direct view onto the operating site. To this end, optical visualization systems/optical implements such as endoscopes or microscopes are available. In order to implement the planning, the medical practitioner needs to create the link between the pre-surgical image data and the intraoperative visual information. As a result of orientation difficulties, this can lead to an extended operation duration or to errors during the operation.

Medical navigation systems are known as orientation aid during the operation. These systems capture the coordinate transforms between the patient and one or more instruments during the operation and visualize these in the pre-surgical planning data. To this end, patient and instrument are equipped with localizers, the position and alignment of which is captured by a measurement system as position capturing apparatus. As measurement systems of a position capturing apparatus, use is made, inter alia, of electromagnetic, optical or ultrasound systems with appropriate sensors, as is also envisaged for the device according to the invention in specific embodiments. The device according to the invention can have an appropriate design. It can comprise appropriate apparatuses for this.

It is known to provide different instruments with localizers for one of such measurement systems, e.g. pointing instruments, suction apparatuses, forceps, needles and the like and to calibrate this instrument such that a coordinate transform to a reference point (generally the instrument tip) is known. The position of the reference point with respect to the anatomy of the patient is displayed on a monitor during the operation in radiological image data of the patient.

Furthermore, in addition to the instruments, which are held directly on a structure, it is also known to provide and calibrate an optical aid, such as an endoscope, with localizers and a device for measuring the distance. As a result, the navigation system captures the position of the endoscope and the device for measuring the distance captures the distance to a structure from a reference point of the endoscope. The combination of the two items of information makes it possible to calculate and present the position of the measurement point, captured contactlessly, in the image data.

It is known that coils with a soft iron core can be used as localizers in electromagnetic measurement systems with alternating fields. Characteristic potential differences are induced into these coils in the alternating field of the so-called field generator of the measurement system, from which characteristic potential differences the position of the coil with respect to the field generator can be established. Since such coils are employed as sensors in an electromagnetic measurement system for capturing the position, they are also referred to as sensor coils.

When presenting the position of the navigated instruments, slice images from a volume data record (e.g. obtained by computed tomography) are often used and the position is plotted into the layer as a point, cross or the like. Three orthogonal planes are often displayed.

As a result of the installation size or as a result of the measurement principle, the known localizers of many measurement systems have to be attached to a part, which remains outside of the patient, of an instrument, the position of which should be captured. As a result, the instrument must have a rigid design in order to ensure an unambiguous transform for the navigation. Hence, it is not possible to navigate flexible instruments using position measuring technology that cannot be attached to the tip of the instrument. Reasons for the attachment outside of the patient may lie in the utilized measurement method, the installation size of the utilized sensor system, insufficient ergonomics by applying the sensor system or a lack of hygiene.

SUMMARY OF THE INVENTION

According to the invention, this object is achieved firstly by a method for presenting image data, secondly by a device for presenting image data and finally also by a medical treatment device, a digital storage medium, a computer program product and a computer program, as defined by the patent claims.

Accordingly, in order to achieve the object, a method for presenting image data is proposed in which an optical implement captures the position and positional information is obtained thus and, with the aid of the positional information, image data are determined and displayed or processed further. Here, the image data to be displayed are at least in part based on virtual image data, not real image data captured directly by the optical implement. These virtual image data represent an object or body part situated in a field of view of the optical implement. Within the scope of the method:

real image data are recorded by means of the optical implement,
the position and/or alignment of the optical implement is captured simultaneously and positional information is derived therefrom; and
the real image data recorded by the optical implement are processed taking into account the positional information to form virtual image data and/or processed together with virtual image data to form image data to be displayed.

Hence virtual image data are generated either from the real image data, for example a three-dimensional model of an object or body part is created from real image data, or real image data, i.e. image data captured by the optical implement, are linked with previously generated virtual image data of the respective object or body part by virtue of, for example, real image data being superposed onto presentations derived from the virtual image data or, vice versa, structures represented by virtual image data being superposed onto imaged real image data. Both can just as easily also be the case, namely that virtual image data are generated from the real image data and real image data are processed in combination with virtual image data to form image data to be displayed.

Here, virtual image data are understood to mean those image data which are not directly recorded by the optical implement but for example were already generated in advance by means of a tomographic method or are present in the form of a three-dimensional model of a respective object or body part. The virtual image data are preferably available in the form of a volume data record, in which the image data are stored associated with coordinates of a volume, i.e. of a virtual space.

Image data to be presented are preferably determined from the virtual image data taking into account the viewing direction of the optical implement, that is to say, for example, those structures represented by the virtual image data which lie in the viewing direction of the optical implement are displayed as image data to be presented.

Processing the image data can include selecting image data to be displayed and/or transforming the image data. Selecting image data is necessary if the virtual image data for example represent a complete body part, but only the image data lying in the viewing direction of the optical implement should be displayed. A transformation of image data is furthermore necessary if a combination of a real object or body part, in which the optical implement is situated, should be brought in line with a coordinate system underlying the virtual image data record. A transformation is also necessary if structures represented by a virtual image data record should be presented with the right perspective in such a way corresponding to the imaging properties of the optical implement with the respective current position and alignment thereof.

In a particularly preferred case, the optical implement is an endoscope. However, in principle, other optical implements can also be considered to be an optical implement within the meaning of the method. Here, optical implements are those implements which record optical images, wherein these images need not necessarily be recorded in the visible wavelength range. By way of example, in order to capture real image data in blood vessels, it may be expedient to obtain real image data with the aid of infrared light in the wavelength range in which blood has a high transparency.

In accordance with a preferred embodiment variant of the method, the method of the recorded real image data includes a photogrammetric evaluation of the real image data in order to obtain a three-dimensional model of the object or body part. This is how volume data records can be obtained from real image data. Preferred embodiment details of this method are explained in more detail elsewhere in this text.

Additionally, or alternatively, the method can be configured in such a way that processing the image data includes a superposition of virtual image data or of structures, features, markings or the like, represented by virtual image data, onto the respective images represented by real image data. Here, it is particularly preferred if contours of object or body structures, which are represented by virtual image data, are superimposed onto real image data. As an example of this, the presentation of vessels branching off from a hollow vessel is described elsewhere in the text.

The method can also, in very general terms, include the selection and processing of virtual image data to form image data to be displayed in such a way that the image data to be displayed reproduce structure boundaries of an object or body part. Such structure boundaries are preferably found in virtual image data taking into account the positional information for the optical implement in such a way that vectors extending in the viewing direction of the optical implement are placed through a space represented by the virtual image data, for example in the form of a volume data record, and a density gradient along a respective vector is analyzed. A high density gradient, i.e. a fast light/dark or dark/light transition, is in this case respectively interpreted as structure boundary of the respectively represented object or body part. In general terms, a high density gradient means a relatively strong change of a variable (such as e.g. image brightness) represented by the virtual image data in a narrow spatial section or on a short path section of a virtual space for example represented by a volume data record.

A device according to the invention for presenting image data comprises an optical implement, a position capturing apparatus for capturing the position of the optical implement, an image data processing apparatus connected to the optical implement and the position capturing apparatus, and a display unit connected to the image data processing apparatus. Here, the image data processing apparatus is preferably configured in such a way that it carries out a method in accordance with one or more of claims 1 to 9.

The image data processing apparatus preferably comprises a storage medium for virtual image data; as a result, the image data processing apparatus is able to access virtual image data directly, which image data are required within the scope of the method according to the invention.

According to the invention, provision is also made for a medical treatment device connected or to be connected to a device in accordance with one of claims 10 to 12 and accordingly preferably to be employed within the scope of a method in accordance with claims 1 to 9.

Likewise, according to the invention, provision is made for a digital storage medium, for example in the form of a disk, CD, DVD or another storage medium known per se, with the storage medium containing control signals that can be read out electrically, configured in such a way that the digital storage medium interacts with a programmable computer system such that automated steps initiate a method according to the invention in accordance with one of claims 1, 2 and 4 to 9.

In the same vein, provision is, according to the invention, also made for a computer program product which contains program code stored on a machine-readable medium, for initiating the automated steps of the method according to the invention in accordance with one of claims 1 to 9 if the computer program product is executed on a computer. Finally, according to the invention, provision is also made in this vein for a computer program.

Further advantageous embodiments of the method of the device are the following:

A digital storage medium according to the invention, more particularly in the form of a disk, CD or DVD with control signals that can be read out electrically, can interact with a programmable computer system in such a way that the automated steps of a method according to the invention are initiated.

In the process, all, some or a few of the automated steps of the method according to the invention can be initiated.

A computer program product according to the invention has program code stored on a machine-readable medium, for initiating the automated steps of the method according to the invention if the computer program product is executed on a computer.

Developments according to the invention are in each case the subject matter of the dependent claims and embodiments.

One aspect, which is also protectable on its own and independently of the presentation of image data, relates to a device for navigation—or, more precisely: positional capture—of the optical implement, which, for example, consists of or at least has a localizer carrier, in particular a coil carrier.

The localizer carrier preferably has a cross section matched to the implement, is hollow in specific embodiments and preferably has low wall strength.

In some embodiments according to the invention, the localizer carrier has a fitting internal diameter such that it can be put over the implement and can be pulled off again. This preferably occurs without a tool being used.

In specific embodiments, hollow coils are wound around the localizer carrier as a coil carrier. The dimensions of the coils and the wire diameter determine the inductance of the coil.

The inductance determines the sensitivity of the measurement system. The coils are contacted by means of wires of a cable, which are laid along the coil carrier. Wireless embodiments are likewise comprised by the present invention.

A casing is applied or pulled over the coils—or differently embodied localizers according to the invention—and the wires (to the extent that these are present) for the purposes of encapsulation from the surroundings.

Herein, "coils" should be understood to mean non-restrictive examples of localizers or sensor coils. A coil carrier should therefore be understood to mean a non-restrictive, special example of a localizer carrier according to the invention.

The casing has a suitable, preferably hollow, round, cross section. In some embodiments, it has low wall strength. Coils and casing are permanently connected to the coil carrier in such a way that the coils and the interspace are encapsulated from the outside. This is advantageous for the hygienic preparation of the device.

The optical visualization systems/optical implements are also described below using the special term endoscope. However, optical implements should not be restricted to endoscopes within the strict sense of the word.

Advantageous developments of the method include navigation attachments for all types of systems and, in particular, optical implements (e.g. laryngoscope, gastroscope but also microscope, etc.) by means of which the medical practitioner looks onto or into the operation site during the operation.

The localizer carrier constitutes a simple employable attachment for, inter alia, endoscopes. In specific embodiments, said localizer carrier only needs to be pushed-on in order to augment an e.g. the endoscope to form a navigated (i.e. equipped with position capturing device or localizer) instrument.

In some embodiments, the localizers are situated arranged concentrically around the instrument, such that the instrument axis is captured without calibration and without decalibration effects.

A localizer (e.g. the coil on the coil carrier) can be situated directly at the instrument tip. The device allows a more compact design of the localizers at the tip compared to all other known localizers. In some embodiments, the instrument with navigation attachment is only minimally thicker.

In further advantageous embodiments, a pipe or a sleeve (closed or partly open in cross section) serves as coil carrier (or, in very general terms, as localizer carrier). The pipe can, for example, be made of metal or plastic.

The casing can, for example, be a pipe. The pipe can, for example, be made of metal or plastic.

The casing and/or the coil carrier can, for example, be a coating which, for example, is produced using CVD, PVD, whirl sintering processes, which are known to a person skilled in the art.

The casing and/or the coil carrier can, for example, be a temperature-formable material (e.g. heat-shrinkable sleeve).

The coil carrier and/or overcoat can both or individually be made of a flexible material (e.g. tubing).

According to the invention, one or more coils can be applied to the coil carrier. In specific embodiments, the surface normal of the coil opening does not correspond with its axis of the instrument or the axis of the coil carrier. As a result, it is advantageously possible to use the coil to capture by meteorological means a vector which is not collinear with the coil axis and/or with the coil-carrier axis.

The surface of the optical implement can also already be used as a coil carrier or localizer carrier.

In an advantageous embodiment, the attachment can be locked into place on the optical implement. By way of example, the attachment can have standard connecting elements, the counterpart of which is on the instrument (e.g. Luer lock connection).

In one advantageous embodiment, the attachment can be used for other instruments in addition to optical implements. By way of example, the use for suction apparatuses or catheters with guide channel is advantageous.

With the aid of the device, i.e. the localizer carrier or attachment, a respective optical visualization system/optical implement becomes a navigated optical instrument in a simple, advantageous manner. As a result, as is conventional in navigation, visualizations of instrument positions in virtual image data can be made possible. It is known to present a navigated instrument in slices of the patient (data record) in a patient coordinate system or a coordinate system formed by the navigated instrument.

In some embodiments according to the invention, the method according to the invention advantageously allows visualizations to be adapted to the operation method and new visualization options to be developed with the aid of the image information from the optical system.

The navigation information is visualized by means of the following method in the virtual image data, i.e. in the virtual space represented by virtual image data. The navigation information is provided to the user by a computational method, which extends the axis of the front-most segment of the instrument in a virtual manner along the "viewing direction". Along this vector created thus (also referred to as viewing vector), a first intersection with the virtual image data of the patient is calculated and hence the point onto which the operator looks is found and visualized in the virtual image data record.

The intersection is found from the gradient of the pixels of the virtual data record along the vector being created. There is a strong gradient (difference in brightness) at the transition from air to tissue. Likewise, the transition from soft tissue to bone can, for example, be assigned by means of a gradient threshold.

In an advantageous embodiment of the invention, a plurality of vectors are used for detecting a plurality of points or lines or surfaces or objects which do not lie in the center of the endoscope. By way of example, use can be made of a beam with two to finitely many virtual rays (viewing vectors) which, for example, form a cone, similar to the cone of vision, extending from the endoscope.

The rays (viewing vectors) can also all lie in one plane.

The intersections of the virtual rays from the endoscope with the virtual image data in the virtual space are calculated by means of e.g. considering the gradient. The visualization can preferably take place in various cross-sectional slice images such that the operator has an overview over all boundary layers of the object in the beam cone.

According to the invention, the slice images (more particularly the three mutually orthogonal slices) can each be aligned with the ray normal.

The slice images (more particularly the three mutually orthogonal slices) can all be aligned with the axis of the instrument.

The slice images (more particularly the three mutually orthogonal slices) can all be aligned with the coordinate definition of the model.

A slice image can be displayed in the plane of the ray and the rays can be plotted as lines.

The visualization of the found lines can take place in known slice images (2.5D presentation).

The presentation can be brought about as 3D model of the captured structures.

Objects can be probed in a further embodiment. Here, the depth information (i.e. the distance between the virtual ray origin and the object—e.g. represented by a boundary layer which manifests itself in the virtual image data by virtue of a high density gradient—along the ray) of the individual rays is used in order to identify objects. If the depth information of adjacent rays is close together, the rays impinge on one object. If the distance is large, one ray lies on one object and the other ray lies on another object. Hence object boundaries are identified. As a result of this, objects can be identified in the virtual model.

Within the meaning of the above-described visualization of virtual image data, the depth information can also be understood to mean the length of the viewing vector from its origin to the "intersection", i.e. to the point at which a density gradient above the gradient threshold is present.

In a further embodiment, objects in the real image data can be detected by the optical visualization system. To this end, these data are digitized (endoscope camera, microscope camera).

Then a slice image can be generated and displayed for each of these objects. By way of example, the slice image can be aligned relative to the image data record, to the instrument or to the principal axis of inertia of the object itself. Objects can be detected and differentiated as a result of several successive items of image data along a movement trajectory. Photogrammetric methods are used to this end. It is feasible that features (e.g. edges) are identified in individual images. As a result of associating the features between several images, it is possible to deduce various objects due to the various movements of the features. To clarify this: the size of an object situated closer changes more quickly than that of an object situated further away. Positional information can be associated with these identified objects on account of the navigation information from the navigated attachment. An object-based 3D model is created from the real image data.

In a further embodiment, the identified objects in the real and virtual model can be used in the state related to one another. By way of example, the virtual model is adapted from the comparison of the associated objects. If, on account of the advance of the operation, an object is missing in the real model, the corresponding object is removed from the virtual model (intraoperative model adaptation). If an object is present in both models but is different in each case, the position of the virtual model can be adapted with the aid of this transformation information (adaptive patient registration).

If it is to be expected that the real objects can move with respect to one another in space (soft tissue), soft tissue movement can be identified from the positional deviation of the models. The virtual model can be adapted accordingly.

The navigated instrument, i.e., for example, the optical implement with position capturing apparatus, which is created by the use of the attachment (optical visualization system with navigation attachment) is used for registering the patient data by means of the described method. Here, several objects in the real image data are associated with virtual objects. By way of example, the nose openings, eye sockets, pinnae are suitable for this purpose. An object known in both models must in this case always be visible and be identified in the real images. The so-called patient localizer is suitable to this end.

The method can also be used to determine the transformation between the virtual model and the real model. As a result of this, it is possible, for example, to present objects, which are not even present in the video image, e.g. planning data (for reconstruction, implants etc.) which are planned in the virtual data record, in the real video image or in the real model. It is likewise possible to present covered structures in the real video image (e.g. branches from arteries, targets regions) in a superposed fashion, for example by virtue of the contours of the covered structures being "plotted" in a real image in the right perspective (for example by means of light or dark lines).

In a further advantageous embodiment of the invention, virtual surface scanning is undertaken over all visible points and the information is then projected onto a suitable reference object, according to methods which are known from e.g. geographic map production. This results in a novel type of presentation. The method can also be applied with lines as a development of a cylindrical projection. By way of example, the suitable reference object can be a simple geometric object such as e.g. a cylinder. However, the reference object can also be a virtual three-dimensional model of an object captured by an optical implement. In both cases, those image data captured by the optical implement and virtual image data are linked together using the positional information.

The visualization of the detected points can also take place in the corresponding video image from a video endoscope or microscope. The imaging properties during the recording of the video image need to have been captured in advance.

As a result of the described projection methods, there is the option of a completely novel way of presenting information (e.g. tunnel rectification). Here, suitable virtual pixels are extracted from the patient image data record by suitable vector arrangements, e.g. circularly or linearly or completely in vessels. The result is then projected onto predefined target structures, e.g. cylinders, spheres, ellipsoids.

Hence, in some embodiments, an advantageous, i.e. adapted to the type of operation, presentation of the navigation information from the navigated instrument becomes possible according to the invention.

BRIEF DESCRIPTION OF THE DRAWINGS

The method according to the invention and the variants thereof, as well as the device according to the invention and further advantageous embodiments of the method and the device can be gathered from the following description of an exemplary embodiment. The attached figures show exemplary aspects of a device according to the invention, specifically.

DETAILED DESCRIPTION

Figure 1:
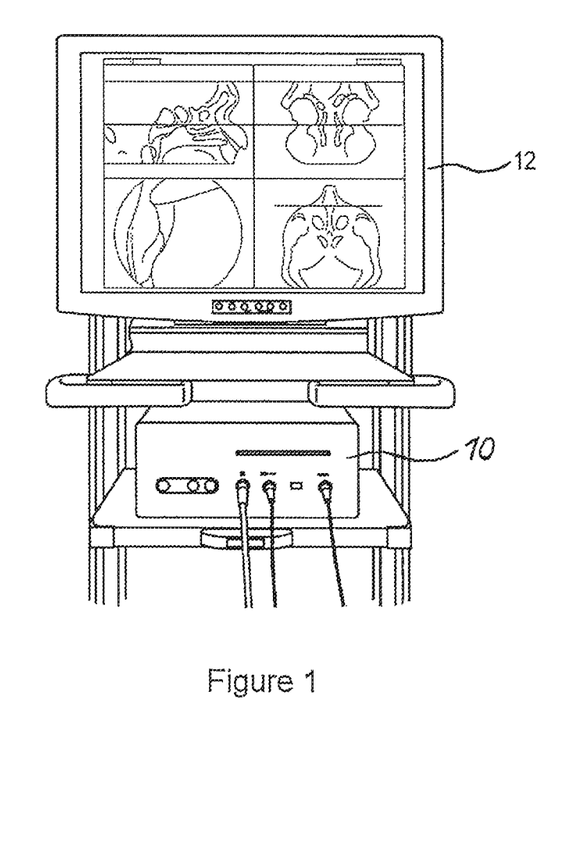
FIG. 1 shows an image data processing apparatus and a display unit connected to the image data processing device.
Figure 2:
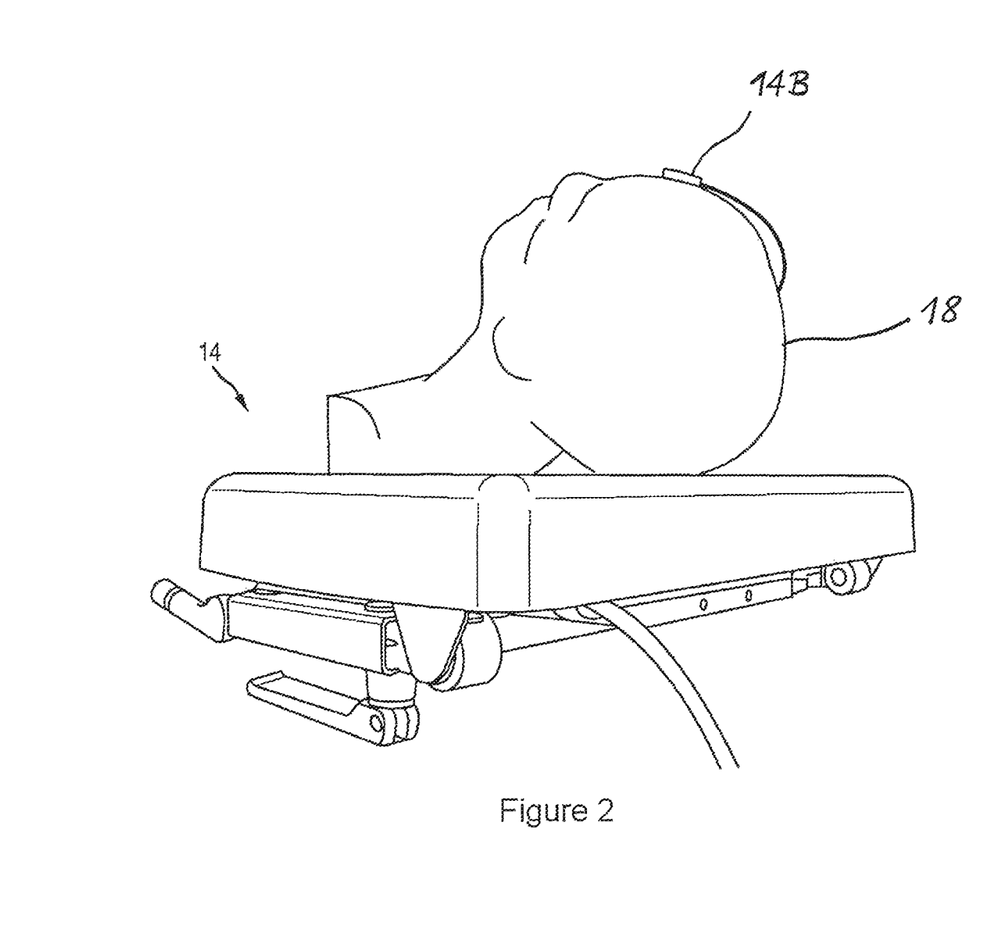
FIG. 2 shows a position capturing apparatus for capturing the position of the optical implement.
Figure 3:
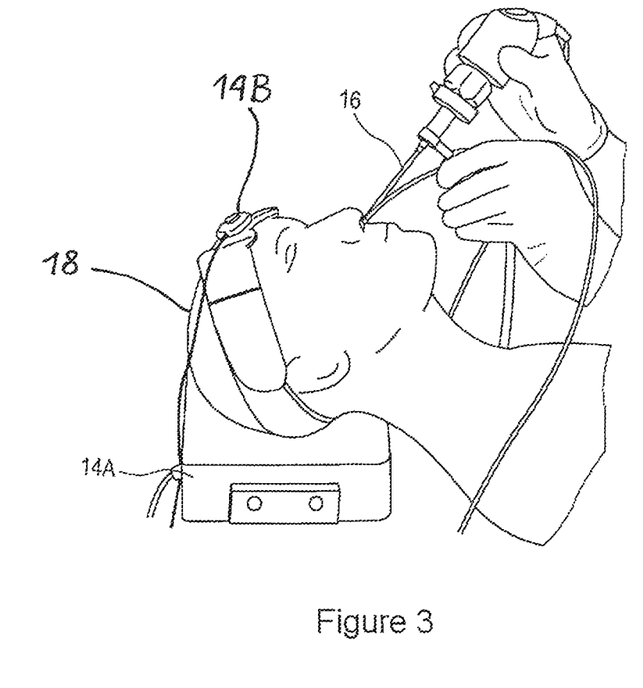
FIG. 3 shows an optical implement and the position capturing apparatus for capturing the position of the optical implement.

FIGS. 1 to 3 show the components of a device according to the invention for presenting image data. The device comprises an image processing apparatus 10, to which, on the output side, a display unit 12 has been connected. On the input side, a position capturing apparatus 14 (see FIGS. 2 and 3) and an optical implement 16 (see FIG. 3), for example an endoscope, are connected to the image processing apparatus 10.

The position capturing apparatus can, in a manner known per se, comprise a field generator 14A for an alternating electromagnetic field and also sensor coils which are attached to the implement whose position should be captured. In this case, the sensor coils are attached (cannot be identified) to the endoscope 16, to be precise, preferably, in the vicinity of the distal end thereof. The sensor coils are preferably small and have a soft magnetic core. Two or three sensor coils are arranged eccentrically with respect to the longitudinal axis of the endoscope 16 at the distal end thereof and have different orientations. As a result of this, it is possible, in a manner known per se, to capture not only the position of the individual coils in the alternating electromagnetic field generated by the field generator 14A but also the orientation, i.e. alignment, thereof. This is how the position capturing apparatus 14 can, at any time, precisely determine both the position and the alignment of, for example, a distal end of the endoscope 16.

The sensor coils are part of the position capturing apparatus and, elsewhere in this text, are also referred to as localizers or—together with their carrier—as position capturing device.

So that this positional information is meaningful with respect to a patient 18, a further sensor coil 14B is attached in a fixed manner on the relevant body part of the patient (in this case the head).

In order to bring virtual image data, i.e., for example, slice images of the patient head obtained by tomography, in line with the instantaneous positions captured by the position capturing apparatus 14, a registration of the body part of the patient—i.e., for example, the head—is initially undertaken, as is likewise known per se. Subsequently an item of positional information respectively obtained by the position capturing apparatus 14 can be associated with a point in the virtual image data, i.e., for example, in corresponding tomographic images of the patient head.

The latter permits a navigation known per se of an instrument by presenting the instrument position in slice images, obtained by tomography, of a body part.

Deviating from or complementing this navigation known per se, the image processing apparatus 10 makes it possible to capture simultaneously real image data recorded by the optical instrument 16 and positional information respectively associated therewith. This means that, for an individual image recorded by the endoscope 16, the positional information is also recorded in each case, which positional information describes the position and alignment of the optical implement 16 at the instant at which the respective individual image was recorded.

This is how the image processing apparatus is able, for example, to link real image data recorded by the optical implement 16 with virtual image data. Such virtual image data can be image data recorded by tomography. However, the virtual image data can also be data of a three-dimensional model of the respective body part.

As a result of this, it is possible, for example, for the image processing apparatus 10 to plot structures into a real image, for example of an elongate hollow organ, recorded by the optical implement 16, which structures would otherwise not be identifiable in the optically recorded image. By way of example, if a hollow organ points away from the hollow organ, which is illustrated in the optically recorded image, at a covered position, the contours of the former hollow organ can be plotted in the right perspective, for example by light or dark lines, in the optically recorded image. By way of example, this would allow an operator to find a branching-off vessel easily, even though said vessel cannot be identified or can only be identified with great difficulty on the basis of real image data recorded by the optical implement.

In an alternative scenario, the device according to the invention for presenting image data can be used to obtain virtual image data representing a 3D model of a body part precisely by virtue of real image data recorded by the optical implement 16 being processed taking into account the respectively associated positional information. To this end, the optical instrument 16 can be moved through, for example, a hollow organ and can, in the process, successively record a sequence of individual images of the hollow organ. Since the individual images were respectively recorded from different positions and alignments, which are however known due to the associated positional information, of the optical implement 16, these individual images show structures of the hollow organ from different perspectives with the aid of characteristic points of the hollow organ which can be recognized in successive individual images. Thus, taking into account the respective positional information, a three-dimensional model of the hollow organ can be constructed using photogrammetry solely on the basis of the real image data and the associated positional information.

In a further step, the image processing apparatus can also be configured in such a way that a three-dimensional model obtained intraoperatively in this fashion can be used by the image processing apparatus 10 to correct a previously produced three-dimensional model, represented by virtual image data, of the body part or hollow organ in real time and to adapt it to the actual conditions. An advantageous embodiment variant of the image processing apparatus therefore remains an intraoperative model adaptation in real time.

Further possible processing of virtual and real, i.e. recorded by the optical implement 16, image data by the image processing apparatus 16, depending on the embodiment variant, consists of the real image data being so to speak projected onto walls in these virtual image data such that a three-dimensional model, for example of a body part or hollow organ, can be presented on the display unit, the surfaces of which model appear precisely in such a way that they correspond in their appearance to the real image data captured by the optical implement 16. Hence, it is possible to present on the display unit 12 a three-dimensional model of the respective body part or hollow organ which has a completely realistic appearance. To this end, the display unit 12 can be a 3D monitor in a particularly advantageous fashion.

The invention claimed is:

1. A method for presenting image data, in which the position of an optical instrument is captured and positional information is obtained thus and, with the aid of the positional information, image data are determined and displayed or processed further, wherein the position of the optical instrument is captured by a position capturing apparatus comprising a field generator for an alternating electromagnetic field and sensor coils which are attached to the instrument,
   wherein the image data to be displayed are at least in part based on virtual image data, which are not captured directly by the optical instrument, which image data represent an object or body part situated in a field of view of the optical instrument, wherein,
   real image data are recorded by the optical instrument,
   the position and/or alignment of the optical instrument is captured simultaneously and positional information is derived therefrom,
   the real image data recorded by the optical instrument are processed taking into account the positional information to form virtual image data and/or processed together with the virtual image data to form image data to be displayed,
   in which the optical instrument has a viewing direction and image data to be presented are determined from the virtual image data taking into account the viewing direction of the optical instrument and wherein covered structures are presented in the real image data in a superposed fashion by virtue of contours of the covered structures being plotted in the real image data in the right perspective.

2. The method as claimed in claim 1, characterized in that the virtual image data are obtained by means of a tomographic method and/or are data of a three-dimensional model of an object or body part.

3. The method as claimed in claim 1, characterized in that processing the image data includes selecting image data to be displayed and/or transforming the image data.

4. The method as claimed in claim 1, characterized in that the optical instrument is an endoscope.

5. The method as claimed in claim 1, characterized in that processing the recorded image data includes a photogrammetric evaluation of the real image data in order to obtain a three-dimensional model of the object or body part.

6. The method as claimed in claim 1, characterized in that processing the image data includes a superposition of virtual image data onto the respective real image data.

7. The method as claimed in claim 6, characterized in that contours of object or body part structures, which are represented by virtual image data, are superimposed onto real image data.

8. The method as claimed in claim 1, characterized in that image data to be displayed are determined taking into account virtual image data in the form of tomographic images and taking into account the viewing direction of the optical instrument by virtue of the fact that viewing vectors corresponding to the viewing direction of the optical instrument are analyzed in the virtual image data so that a stronger density gradient along a respective viewing vector is interpreted as a structure boundary of the respectively represented object or body part.

9. A device for presenting image data, comprising:
   an optical instrument,
   a position capturing apparatus for capturing the position of the optical instrument, wherein the position of the optical instrument is captured by a position capturing apparatus comprising a field generator for an alternating electromagnetic field and sensor coils which are attached to the instrument,
   an image data processing apparatus connected to the optical instrument and the position capturing apparatus, and
   a display unit connected to the image data processing device,
   wherein the image data to be displayed are at least in part based on virtual image data, which are not captured directly by the optical instrument, which image data represent an object or body part situation in a field of view of the optical instrument, wherein
   the optical instrument is configured to record the real image data,
   the image data processing device is configured so that the position and/or alignment of the optical instrument is captured simultaneously and positional information is derived therefrom, and
   the image data processing device is configured so that the real image data recorded by the optical instrument are processed taking into account the positional information to form virtual image data and/or processed together with the virtual image data to form image data to be displayed,
   in which the optical instrument has a viewing direction and wherein the image data processing unit is configured so that image data to be presented are determined from the virtual image data taking into account the viewing direction of the optical instrument and wherein covered structures are presented in the real image data in a superposed fashion by virtue of contours of the covered structures being plotted in the real image data in the right direction.

10. The device as claimed in claim 9, characterized in that the image data processing device comprises a storage medium for virtual image data.

11. The device as claimed in claim 9, wherein the position capturing apparatus comprises a field generator and sensor coils, the sensor coils attached to the optical instrument.

12. A digital storage medium, in the form of a disk, CD or DVD, with control signals read out electrically, configured to interact with a programmable computer system in such a way that the automated steps of claim 1 are initiated.

13. A computer program product with program code stored on a non-transitory machine-readable medium, which when executed on a computer initiate the automated steps of claim 1.

14. A computer program with program code stored on a non-transitory machine-readable medium, which when executed on a computer initiate the automated steps of a method according to claim 1.

* * * * *